United States Patent [19]

Kulp

[11] Patent Number: 4,961,499

[45] Date of Patent: Oct. 9, 1990

[54] HEMOSTATIC CLIP CARTRIDGE

[75] Inventor: Rodney Kulp, Harleysville, Pa.

[73] Assignee: Pilling Co., Fort Washington, Pa.

[21] Appl. No.: 461,116

[22] Filed: Jan. 4, 1990

[51] Int. Cl.$^5$ .............................................. B65D 85/00
[52] U.S. Cl. ...................................... 206/339; 206/340
[58] Field of Search ............................... 206/338–348; 606/139, 151, 157

[56] References Cited

U.S. PATENT DOCUMENTS

| | | |
|---|---|---|
| 3,270,745 | 9/1966 | Wood . |
| 3,326,216 | 6/1967 | Wood . |
| 3,363,628 | 1/1968 | Wood . |
| 3,439,522 | 4/1969 | Wood . |
| 3,631,707 | 1/1972 | Miller . |
| 3,713,533 | 1/1973 | Reimels .................. 206/339 |
| 4,076,120 | 2/1978 | Carroll et al. ........... 206/339 |
| 4,212,390 | 7/1980 | Raczkowski et al. ..... 206/339 |
| 4,294,355 | 10/1981 | Jewusiak et al. ......... 206/339 |
| 4,361,229 | 11/1982 | Mericle .................. 206/341 |
| 4,397,312 | 8/1983 | Molko . |
| 4,416,130 | 3/1979 | Samuels et al. .......... 206/338 |
| 4,685,564 | 8/1987 | Hills et al. .............. 206/341 |
| 4,696,396 | 9/1987 | Samuels ................. 206/339 |

Primary Examiner—Jimmy G. Foster
Attorney, Agent, or Firm—Howson & Howson

[57] ABSTRACT

A cartridge for holding and dispensing hemostatic clips, comprises a plurality of generally U-shaped hemostatic clips, and a unitary, molded cartridge body having clip-receiving slots with internal clip-supporting posts, and retaining projections in each slot formed on the opposed walls defining the slot. The retaining projections are located adjacent to the top of the post within the slot and extend toward the opposite wall. Each retaining projection has a clip-engaging surface and is tapered so that it gradually increases in thickness, from a narrow bottom portion adjacent the top of the post means to a wider intermediate portion above the narrow bottom portion, so that the clip engaging surface overhangs the post to provide secure retention of the clip in the slot.

6 Claims, 1 Drawing Sheet

HEMOSTATIC CLIP CARTRIDGE

BRIEF SUMMARY OF THE INVENTION

This invention relates to surgery and in particular to an improved cartridge for holding and dispensing preformed, generally U-shaped hemostatic clips used for occluding blood vessels in surgery.

In recent years hemostatic clips have been developed which provide rapid and efficient means for closing off blood vessels during surgery. Typical hemostatic clips are generally U-shaped clips formed from a soft, non-springy metal. These clips are supplied in a molded cartridge having a row of slots, with one clip in each slot. The clips are individually removed from their slots, when needed, by a pliers-like clip applicator. When pressed into a slot in the cartridge, the clip applicator automatically grips the clip securely so that the clip can be removed from the slot and held by the applicator. The applicator is then used to position the U-shaped clip over a blood vessel and to compress the legs of the clip together so that the blood vessel is closed off. Afterward, the applicator is disengaged from the clip and may be used to remove another clip from the cartridge.

These developments are described in detail in the following U.S. Pat. Nos.: E. C. Wood 3,270,745, 3,326,216, 3,363,628, 3,439,522; A. K. Miller 3,631,707; H. G. Reimels 3,713,533; R. L. Carroll et al. 4,076,120; P. B. Samuels et al. 4,416,130; W. P. Molko 4,397,312; and P. B. Samuels 4,696,396.

A typical clip applicator, as shown in Wood U.S. Pat. No. 3,326,216, has a pair of relatively movable jaws, each of which has a blind groove. The grooves receive the legs of a clip, and ridges at the end of the blind grooves engage the ends of the legs of the clip to provide for positive removal of the clip from its cartridge. In Wood, U.S. Pat No. 3,326,216, the clip is held in a slot in the cartridge with its legs in engagement with the opposite sides of a post, and with its connecting portion held frictionally between parallel, opposed surfaces located above the top of the post. This structure allows the cartridge to hold the clip in place while providing clearance within the slots for reception of the jaws of the clip applicator.

The cartridge described in Samuels, U.S. Pat. No. 4,696,396 uses two spaced, parallel ribs on each of the opposed walls of a slot to engage the clip while allowing clearance for entry of the applicator into the slot. The cartridge structure described in the Samuels patent is intended to keep the clips secured in the cartridge while making them freely accessible when it is desired to remove them for use.

Prior hemostatic clip cartridges, if constructed in such a way as to hold the clips securely against accidental release, have made clip removal difficult or have been structurally complex. The principal object of this invention is to provide a simple hemostatic clip cartridge which securely holds the clips against accidental removal, but which allows easy removal of the clips by means of a clip applicator during surgery. Other objects of the invention include ease of manufacture of the cartridge, ease of loading of the cartridge, and easy and reliable removal of clips from the cartridge during surgery.

The cartridge in accordance with the invention is intended to hold and dispense pre-formed, generally U-shaped hemostatic clips, where each clip has a pair of legs and a connecting portion extending from one leg to the other. The cartridge comprises a unitary molded cartridge body having: (a) an elongated base; (b) a plurality of parallel walls extending upwardly from the base and having faces extending transverse to the direction of elongation of the base and spaced from each other to define a series of clip-receiving slots between adjacent walls; (c) a post having a top and two sides, within each of the slots for supporting a clip with one leg of the clip on one side of the post, the other leg of the clip on the opposite side of the post, and the connecting portion engaged with the top of the post; and (d) at least one retaining projection having a clip-engaging surface in each slot formed on one of the walls defining the slot and extending adjacent to the top of the post within the slot toward the opposite wall defining the slot. The cartridge of the invention is characterized by the fact that its retaining projection is tapered so that it gradually increases in thickness, measured in a direction parallel to the direction of elongation of the cartridge base, from a narrow bottom portion adjacent the top of the post to a wider intermediate portion above the narrow bottom portion, whereby the clip engaging surface overhangs the post to provide secure retention of a clip in the slot.

In a preferred form of cartridge constructed in accordance with the principles of the invention, each slot has two substantially identical, opposed retaining projections.

Also, in the preferred cartridge, the wall faces defining each slot converge in a direction toward the base to provide a tapered slot.

In the preferred cartridge, to facilitate loading of the clips into the cartridge during manufacture, the portion of each of the first and second retaining projections located above its wider intermediate portion, gradually decreases in thickness, measured in a direction parallel to the direction of elongation of the cartridge base, from the wider intermediate portion toward the uppermost part of the retaining projection.

The retaining projections are preferably centrally located on the faces of the slot-defining walls of the cartridge, adjacent to slots formed in the tops of the walls, so that the projections are located at the points of maximum resiliency of the walls.

Other objects, details and advantages of the invention will be apparent from the following detailed description, when read in conjunction with the drawings.

DETAILED DESCRIPTION

Figure 2:
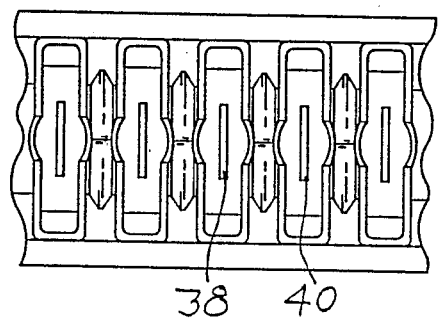
FIG. 2 is a fragmentary top plan view of the cartridge of FIG. 1.

The cartridge, as shown in the drawings, is a unitary, relatively rigid, element, injection molded from a suitable synthetic resin such as polyethylene. It comprises a base 4 which is elongated as shown in FIG. 2, and a series of uniformly spaced walls 5, 6, 7, 8 and 9 which extend upwardly from an upper portion 10 of the base. The walls extend transverse to the direction of elongation of the cartridge base and their faces define a series of uniformly spaced, clip-receiving slots 11, 12, 13 and 14.

Figure 1:
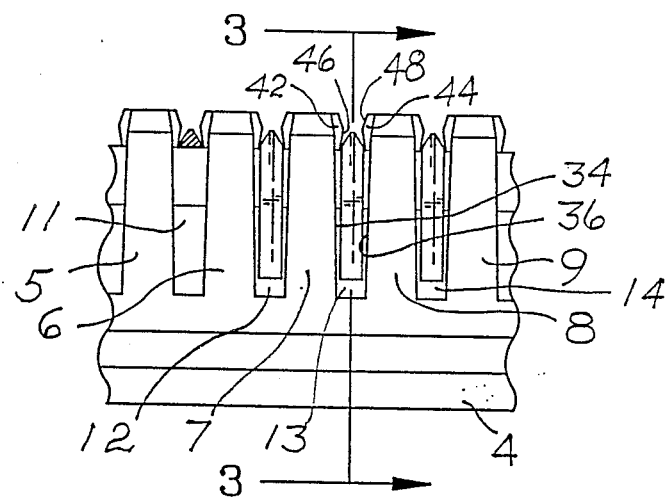
FIG. 1 is a fragmentary side elevation of a cartridge in accordance with the invention showing four clips in place, one of the clips being shown in section.
Figure 3:
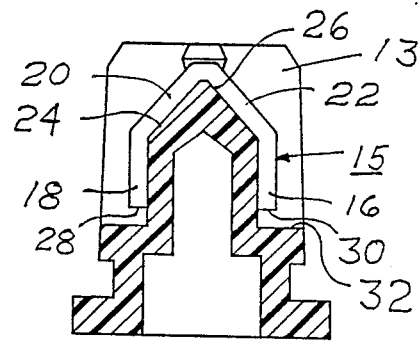
FIG. 3 is a vertical section taken on plane 3—3 indicated in FIG. 1.

The cartridge may have any desired number of slots, and FIGS. 1, 2, and 3 show only a part of the total number of slots in the cartridge. The cartridges are disposable, and each cartridge is provided in sterilized packaging for use only in a single surgical operation. Cartridges may be provided in several different sizes in order to allow the surgeon to select a cartridge with the desired number of clips.

A typical hemostatic clip 15 is shown in FIG. 3. The clip is pre-formed in the shape shown and has two legs, 16 and 18, which extend generally parallel to each other, and a connecting portion comprising elements 20 and 22 which extend between the upper ends of legs 16 and 18 so that the clip is generally in the shape of an inverted "U". The clip is formed of soft, non-springy metal, and is adapted to be applied to a blood vessel by means of an applicator such as the one described in Wood U.S. Pat. No. 3,326,216, dated June 20, 1967. The applicator of the Wood patent is a pliers-like instrument having opposed, jaws with blind grooves adapted to receive the legs of a clip. Ridges are provided at the ends of the grooves for engagement with the lower ends of the clip legs to provide for positive engagement of the clips with the jaws of the applicator. The entire disclosure of the Wood patent is here incorporated by reference.

The cartridge includes molded clip-receiving posts in each slot, the post for slot 13 being shown at 24 in FIG. 3. The post conforms generally to the shape of the clip and the upper portion 26 of the post holds the clip in a position such that the lower ends 28 and 30 of its legs are spaced above floor 32 of slot 13. This allows the legs 16 and 18 of the clip to be received in the grooves of the clip applicator jaws, with the ridges at the ends of the blind grooves positioned underneath the ends 28 and 30 of the clip legs.

As shown in FIG. 1, the slots of the cartridge are wider than the clips to allow clearance for the applicator jaws. Preferably, the opposed, slot-defining faces of the walls, e.g. faces 34 and 36, converge in a direction toward base 4 to provide a tapered slot. This permits the faces of the walls to limit movement of the lower ends of the clips in directions parallel to the elongation of the base, while permitting easy entry of a set of clip applicator jaws having the shape of the applicator jaws shown in Wood U.S. Pat. No. 3,326,216.

Each wall has a centrally located slot formed in its upper end, the slots for walls 7 and 8 being indicated at 38 and 40 in FIG. 2. These slots provide relief to prevent deformation of the cartridge during sterilization. They also provide the wall with a degree of compressibility. The invention takes advantage of the compressibility of the walls to hold the clips in place.

In order to hold the clips in place securely, while providing adequate clearance in the clip-receiving slots for entry of the applicator jaws, retaining projections are provided on both of the opposed faces defining each slot. The retaining projections for slot 13 are indicated at 42 and 44. Each retaining projection is formed with a clip-engaging surface, the clip-engaging surface for projection 42 being indicated at 46. The lower portion of the projection, i.e. the portion having the clip-engaging surface is tapered so that it gradually increases in thickness, measured in a direction parallel to the direction of elongation of cartridge base 4, from a narrow bottom portion adjacent the top of the post 24 to a wider intermediate portion above the narrow bottom portion. The clip-engaging surfaces of the opposed projections 42 and 44 overhang the post to provide secure retention of clip 15 in the slot. The upper portions 48 of the projections are also tapered to facilitate loading of the clips into the cartridge.

During removal of a clip, using a clip applicator, the retaining projections holding the clip move outwardly as a result of the camming action of the clip against the tapered clip-retaining surfaces. Slots 38 and 40 in the walls permit this movement to take place easily, by providing the central portions of the walls adjacent to the clip-retaining projections with a high degree of resiliency. Thus, with the clip-retaining projections centered on the walls, it takes little effort to remove the clips, yet they are held in place securely.

Various modifications can be made to the clip cartridge described. For example, the resilience necessary to permit clip removal can be achieved by choice of appropriate compressible materials for molding the cartridge, thereby eliminating the central slots in the tops of the walls. Many other modifications, which will occur to persons skilled in the art, may be made without departing from the scope of the invention as defined in the following claims.

I claim:

1. A cartridge for holding and dispensing pre-formed, generally U-shaped hemostatic clips, each clip having a pair of legs and a connecting portion extending from one leg to the other, the cartridge comprising a unitary molded cartridge body having: an elongated base; a plurality of parallel walls extending upwardly from the base and having faces extending transverse to the direction of elongation of the base and spaced from each other to define a series of clip-receiving slots between adjacent walls; post means, having a top and two sides, within each of the slots for supporting a clip with one leg of the clip on one side of the post means, the other leg of the clip on the opposite side of the post means, and the connecting portion engaged with the top of the post means; and at least one retaining projection in each slot formed on one of the walls defining the slot and extending adjacent to the top of the post means within the slot toward the opposite wall defining the slot; the retaining projection having a clip-engaging surface and being tapered so that it gradually increases in thickness, measured in a direction parallel to the direction of elongation of the cartridge base, from a narrow bottom portion adjacent the top of the post means to a wider intermediate portion above the narrow bottom portion, whereby the clip engaging surface overhangs the post means to provide secure retention of a clip in the slot.

2. A cartridge according to claim 1 in which each slot has, on the wall opposite said one of the walls, a second retaining projection opposed to said one retaining projection.

3. A cartridge according to claim 1 in which each slot has, on the wall opposite said one of the walls, and a second retaining projection opposed to said one retaining projection, said second retaining projection also having a clip-engaging surface tapered so that it gradually increases in thickness, measured in a direction parallel to the direction of elongation of the cartridge base, from a narrow bottom portion adjacent the top of the post means to a wider intermediate portion above the narrow bottom portion, whereby the clip engaging surface of the second retaining projection also overhangs the post means, and both retaining projections in the slot provide secure retention of a clip in the slot.

4. A cartridge according to claim 1 in which the wall faces defining each slot converge in a direction toward the base to provide a tapered slot.

5. A cartridge according to claim 1 in which each slot has, on the wall opposite said one of the walls, a second retaining projection opposed to said one retaining projection, said second retaining projection also having a clip-engaging surface and being tapered so that it gradually increases in thickness, measured in a direction parallel to the direction of elongation of the cartridge base, from a narrow bottom portion adjacent the top of the post means to a wider intermediate portion above the narrow bottom portion, whereby the clip engaging surface of the second retaining projection also overhangs the post means, and both retaining projections in the slot provide secure retention of a clip in the slot, and in which the portion of each of said first and second retaining projections located above its wider intermediate portion, gradually decreases in thickness, measured in a direction parallel to the direction of elongation of the cartridge base, from said wider intermediate portion toward the uppermost part of the retaining projection.

6. A cartridge for holding and dispensing hemostatic clips, comprising a plurality of generally U-shaped hemostatic clips, each clip having a pair of legs and a connecting portion extending from one leg to the other, and a unitary molded cartridge body having: an elongated base; a plurality of parallel walls extending upwardly from the base and having faces extending transverse to the direction of elongation of the base and spaced from each other to define a series of clip-receiving slots between adjacent walls, there being one of said clips in each clip-receiving slot; post means, having a top and two sides, within each of the slots, each post means supporting one of said clips with one leg of the clip on one side of the post means, the other leg of the clip on the opposite side of the post means, and the connecting portion engaged with the top of the post means; and at least one retaining projection in each slot formed on one of the walls defining the slot and extending adjacent to the top of the post means within the slot toward the opposite wall defining the slot; the retaining projection having a clip-engaging surface and being tapered so that it gradually increases in thickness, measured in a direction parallel to the direction of elongation of the cartridge base, from a narrow bottom portion adjacent the top of the post means to a wider intermediate portion above the narrow bottom portion, whereby the clip engaging surface overhangs the post means to provide secure retention of the clip in the slot.

* * * * *